United States Patent [19]

Brady

[11] Patent Number: 5,002,057
[45] Date of Patent: Mar. 26, 1991

[54] COVER FOR PRISM OF AN APPLANATION TONOMETER AND METHOD OF APPLICATION THEREOF

[75] Inventor: Steven E. Brady, Cherry Hill, N.J.

[73] Assignees: G. L. Spaeth; Eye Disease Foundation, both of Philadelphia, Pa.; part interest to each

[21] Appl. No.: 138,200

[22] Filed: Dec. 28, 1987

[51] Int. Cl.$^5$ ........................ A61B 3/16; B65B 85/08
[52] U.S. Cl. ...................................... 128/652; 206/69
[58] Field of Search .............................. 128/645–652, 128/736; 604/263; 206/69

[56] References Cited
U.S. PATENT DOCUMENTS

| | | | |
|---|---|---|---|
| 3,443,421 | 5/1969 | Posner et al. | 128/652 |
| 3,511,085 | 5/1970 | Posner et al. | 128/652 |
| 3,833,115 | 9/1974 | Schapker | 128/736 X |
| 3,878,836 | 4/1975 | Twentier | 128/736 X |
| 3,913,390 | 10/1975 | Piazza | 128/652 |
| 4,213,464 | 7/1980 | Katz et al. | 128/652 X |
| 4,619,271 | 10/1986 | Burger et al. | 128/736 |
| 4,662,360 | 5/1987 | O'Hara et al. | 128/736 X |

OTHER PUBLICATIONS

Goldmann Applanation Tonometer Brochure.

Primary Examiner—Max Hindenburg
Assistant Examiner—Robin R. Longo
Attorney, Agent, or Firm—Siegmar Silber

[57] ABSTRACT

A sterile and disposable cover for the prism of an applanation tonometer or similar device functions to preclude the transfer of microorganisms from the eye of a patient to the prism during an examination. The prism is a rearwardly diverging frustoconical configured member with a flat forwardly disposed face, and the cover includes a conformable barrier and a removable holder. The cover has a body of substantially optically transparent material for deposition upon the flat forwardly disposed face; and a side portion contiguous with the body portion. The side portion clings resiliently to the prism wall forming a seal therewith. Optionally, there are provided tab portions attached to the outer edges of the side portion, which tabs faciltate the removal of the disposable cover. The removable holder is used for depositing the barrier upon the holder includes a carrier strip releasably adhered to the barrier, with an aperture in the carrier strip for exposing the body portion and for receiving the face of the prism. This enables insertion of the prism through the aperture so that the face is emplaced on the body portion of the cover. To maintain sterility, an aperture cover is removably secured to the carrier strip on the side opposite the barrier. The aperture cover is demountable from the barrier and may be demounted without disturbing the mechanical barrier. Further, a sterile seal attached to the carrier strip completes the safeguarding of the barrier.

20 Claims, 2 Drawing Sheets

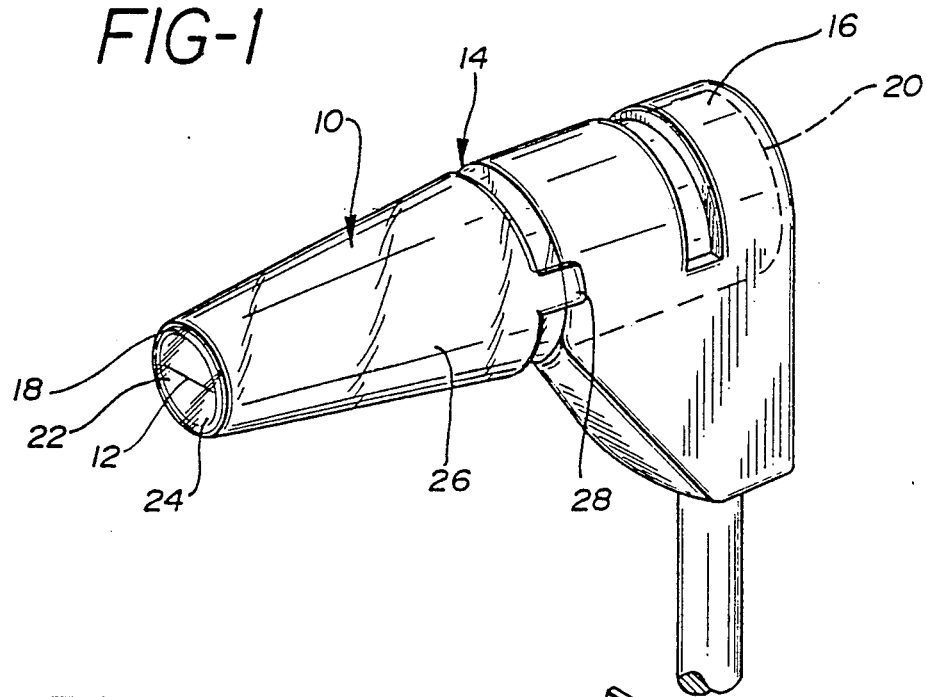
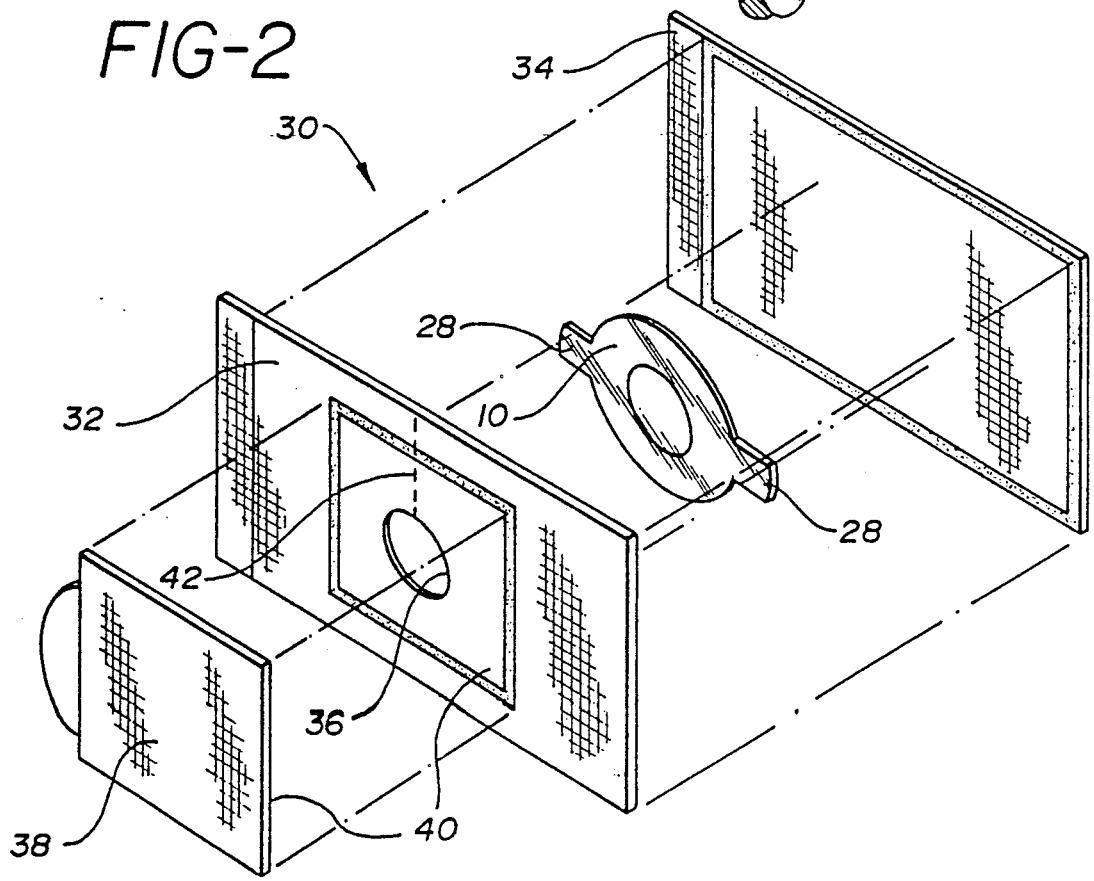

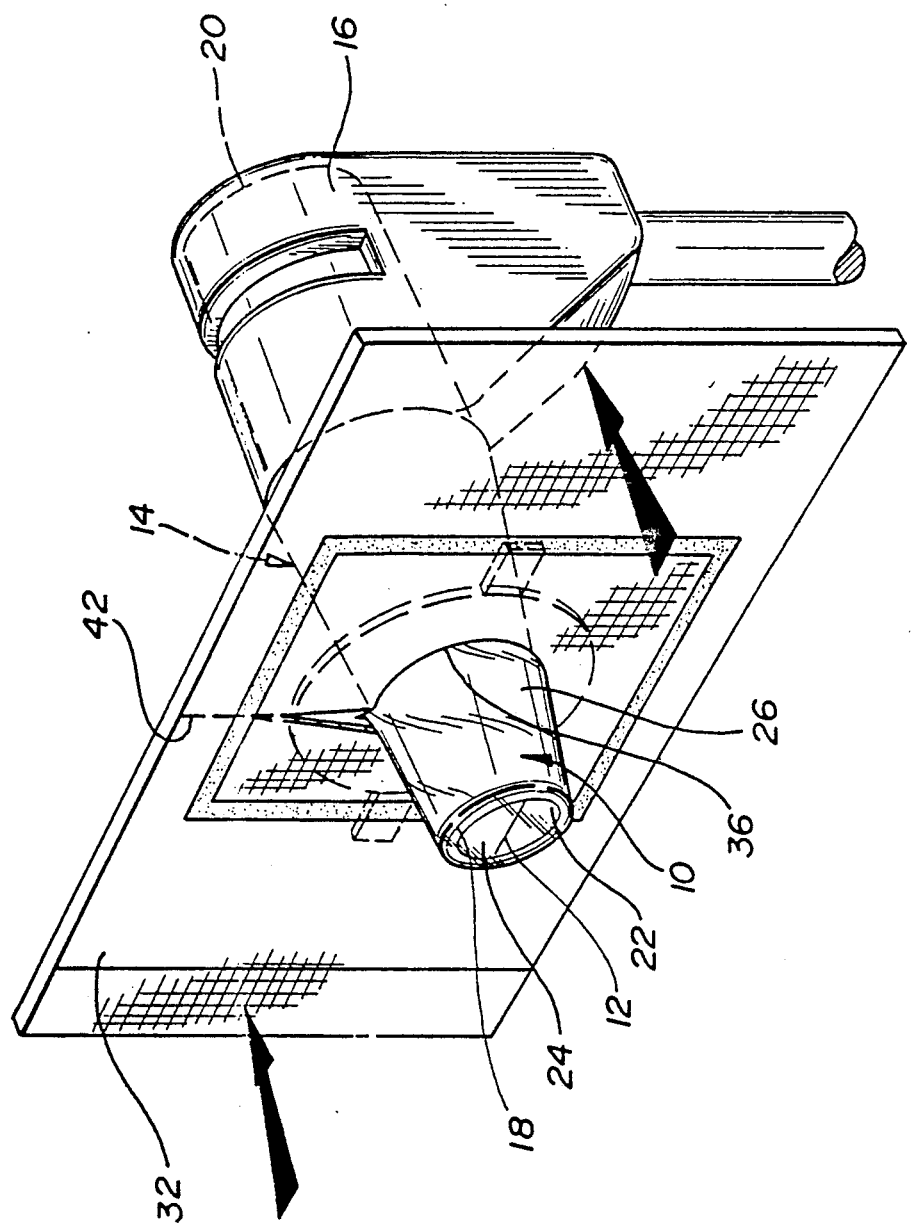

COVER FOR PRISM OF AN APPLANATION TONOMETER AND METHOD OF APPLICATION THEREOF

BACKGROUND OF THE INVENTION

1. Field of the Invention

This invention relates to ophthalmological devices, and more specifically to a new sterile cover for the prism of an applanation tonometer or a similar device and, a packaging device for the sterile cover. Further, the invention relates to a method of mounting the cover onto the prism without human contact with the sterile area and of dismounting the cover from the prism without human contact with the area of the cover that has potentially been exposed to infectious disease microorganisms.

2. Disclosure of the Prior Art

The invention hereof is discussed within the bounds of the medical technology surrounding the Goldmann applanation tonometer, the technic for using the same, and the medical literature arising from the application thereof. The Goldmann applanation tonometer is an ophthalmological instrument, described in U.S. Pat. No. 3,070,997 to Papritz, Goldmann and Schmidt and assigned to Haag-Streit AG, Bern, Switzerland. The instrument is principally manufactured by the assignee whose product literature entitled, "Goldmann Applanation Tonometer Model T900, R900, 1080 and 870" is further descriptive of the present-day technology and thereby provides a background against which the present invention can be more readily understood.

The need for new sterile ophthalmic technics has been urged in recent years as the understanding has grown of the communicable nature of viral and bacterial infections. Few practicing opthalmologists have not at sometime been unfortunate enough to have a patient return to their office with an eye infection which was likely contracted during a previous examination. Even in an office where meticulous hand washing and other good hygiene rules are maintained, patients are still at risk for contracting an infectious disease. In ophthalmic practice, it is believed that communication of infectious disease is likely to occur during applanation tonometry as the tonometer prism is the only instrument that comes into direct contact with the patient's eye during a routine examination. Medical literature has documented the presence of various viruses on tomometer prisms including adenovirus type 8, herpes simplex virus type 1 and hepatitis B surface antigen. Refer to Craven et al, "Applanation tonometer tip sterilization for adenovirus type 8, *Opthalmology* 1987; Ventura et al, "Viability of herpes simplex virus type 1 on the applanation tonometer," *American Journal of Opthalmology (AJO)* 103:48, 1987; and, Moniz et al, "Removal of hepatitis B surface antigen from a contaminated applanation tonometer," *AJO*, 91:522-525, 1981.

The rising incidence of the Acquired Immune Deficiency Syndrome (AIDS), has stimulated much renewed concern regarding the spread of infection by applanation tonometry. AIDS has been found to be caused by the human immunodeficiency virus (HIV) which was previously thought to be transmitted only by sexual and direct intravenous routes. However, a recent report describes an AIDS laboratory worker showing positive HIV serology with no history of these risk factors To date there have been no reported studies of HIV and tonometer prisms or cases of AIDS being transmitted via applanation tonometry. However, this theoretical possibility does exist as HIV has been isolated from human tears, corneal tissue and conjunctival epithelium. Of greatest concern is the recent evidence indicating that AIDS can be contracted by exposure of intact mucous membranes such as the lips and mouth to the virus. This raises the distinct probability that AIDS could be communicated from one patient to another by applanation tonometry. Refer to Schuman et al, "Acquired immunodeficiency syndrome (AIDS)," *Survey of Ophthalmology* 31:384-410, 1987; Fujikawa et al, "Isolation of human T-cell leukemia/lymphotopic virus type III (HTVBL-III) from the tears of a patient with acquired immunodeficiency syndrom," *Lancet* 2:529-530, 1985; Salahuddin SA, et al, "Isolation of the human T-cell leukemia/lympotropic virus type III from the cornea," *AJO* 101:149-152, 1986; and, Fujikawa et al, "Human T0cell leukemia/lymphotropic virus type III in the conjunctival epithelium of a patient with AIDS," *AJO* 100:507-509, 1985.

Various methods have been utilized in the past to reduce the risk of transmitting infectious disease via applanation tonometry. These range from wiping the prism with various substances to removing the prism and storing it in a disinfecting solution. Although some of these methods have, when used correctly, been shown to sterilize effectively the tonometer prism, several shortcomings are still present which prevent these methods from providing the optimal solution. To sterilize the tonometer prism effectively by wiping the prism while still in its holder with a disinfectant solution precludes the minimum 5 minute disinfectant exposure recommended by the Center for Infectious Diseases in Atlanta (refer to: *Morbidity & Mortality Weekly Report*, 34:533-4, 1985).

Unless all disinfectant is removed from the tonometer surface prior to measuring intraocular pressure, the residual disinfectant will cause toxic corneal epithelial damage. Removal of disinfectant requires rinsing the prism with sterile saline or water. Additionally, according to the manufacturer, damage to tonometer prisms may result from application of alcohol. Furthermore, repeated mechanical cleaning reduces the smoothness of the prism; such small scratches and pits may shield microorganisms from the disinfectant. Moreover, they reduce the accuracy of the instrument. Sterilization technics requiring removal of the tonometer prism from its holder, while superior in terms of disinfection are less convenient and therefore less likely to be employed in a busy office setting. These technics require removal of the prism, placement in a container which may contain a substance toxic to the skin and a wait of 5-10 minutes for adequate disinfection. The prism is then stored. Corboy et al reports that Shapiro has suggested wrapping the prism in transparent strips of plastic household film. The prism must then be rinsed in sterile saline or water and dried before being reinserted into the prism holder. If this system is employed, more than one prism must be on hand to rotate through the system. Also, unless sterile gloves and a sterile drying cloth are used the potential exists for re-contamination while inserting the prism back into its holder. Refer to Corboy et al, "Mechanical sterilization of the applanation tonometer," *AJO*, 71:889-91, 1971.

With these prior art methods, direct contact between the tonometer prism and the precorneal tear film is still necessary to measure accurately the intraocular pressure. As a result of the direct contract, the possibility always exists for contamination, especially as no mechanical barrier to infectious microorganisms has been employed.

SUMMARY

The described invention discloses a sterile and disposable cover for the prism of an applanation tonometer or similar device which cover precludes the transfer of microorganisms from the eye of a patient to the prism during an examination. The prism is a rearwardly diverging frustoconical configured member with a flat forwardly disposed face, and the cover includes a conformable barrier and a removable holder. The cover has a body of substantially optically transparent material for deposition upon the flat forwardly disposed face; and a side portion contiguous with the body portion. The side portion clings resiliently to the prism wall forming a seal therewith. Optionally, there are provided tab portions attached to the outer edges of the said portion, which tabs facilitate the removal of the disposable cover. The removable holder is used for depositing the barrier upon the prism while substantially excluding air from between the barrier and the face of the prism. In the disclosed devices the removably holder includes a carrier strip releasable adhered to the barrier, with an aperture in the carrier strip for exposing the body portion and for receiving the face of the prism. This enables the insertion of the prism through the aperture so that the face is emplaced on the body portion of the cover. To maintain sterility, an aperture cover is removably secured to the carrier strip on the side opposite the barrier. The aperture cover is demountable from the barrier and may be demounted without disturbing the mechanical barrier. Further, a sterile seal attached to the carrier strip completes the safeguarding of the barrier and the sterile seal, the carrier strip and the aperture cover form a sealed envelope about the barrier precluding contact thereby with microorganisms. When the sterile cover is used, prior to a tonometric examination, the sterile cover is deposited onto the prism without operator contact with the sterile body and side portions of the barrier device, and, after a tonometric examination, the contaminated cover is removed from the prism without the microorganisms thereon being transferred to the operator. In addition to the device, a sterile technic for utilizing the barrier is discussed herein.

BRIEF DESCRIPTION OF THE DRAWINGS

FIG. 1 is a perspective view of the disposable cover of this invention mounted on a prism of an applanation tonometer.

FIG. 2 is an exploded view of the disposable cover, an envelope structure therefor; and, FIG. 3 is an illustration of the mounting of the disposable cover of this invention upon the prism of an applanation tonometer.

DESCRIPTION OF THE PREFERRED EMBODIMENT

The disclosed invention is more clearly understood upon acquiring a basic knowledge of the applanation tonometer, an ophthalmic instrument for measurement of intraocular pressure (IOP). The instrument correlates the force required to flatten or applanate the cornea with the fluid pressure inside the eye. In the Goldmann applanation tonometer, a frustoconical prism mounted on a pressure arm, a slit lamp, and a binocular microscope are used to ascertain when the desired degree of applanation is obtained. A pattern (mires) of the application of sufficient force is illuminated by the slit lamp and is observable on the face of prism by viewing through the microscope. A guage is then read which provides the IOP in millimeters of mercury (mm. of Hg).

Referring now to FIG. 1, the disposable cover of this invention is shown and is referred to generally by reference numeral 10. The disposable cover 10 is emplaced on prism 12 of applanation tonometer 14. While shown only schematically, the tonometer 14 includes a pressure arm 16 upon which prism 12 is mounted. The prism 12 has a forwardly disposed face 18 and a rearwardly diverging frustoconical side portion 20. For purposes of this application, the forward end of the prism is that end which during tonometry is emplaced on the cornea of the eye of the patient, and, conversely, the rearward end of the prism is the opposite end which is held by the pressure arm. The disposable cover 10 is constructed to form a conformable barrier 22 which precludes the transfer of microorganisms from the eye of a patient to the prism or from the prism to the patient during a tonometric examination. The comfortable barrier 22 has a body portion 24 and continguous therewith a side portion 26. The body portion 24 is constructed from a substantially optically transparent material and for deposition upon the face 18 of prism 12. The side portion 26 of the conformable barrier 22 is constructed to stretch circumsiliently or, in other words, circumferentially resiliently cling without the aid of an adhesive, but merely by the physical properties of the side portion 26 material to the rearwardly diverging side 26 of prism 12. Optionally, the conformable barrier 22 is constructed to include tab portions 28 for protection of the instrument operator or the installer of the barrier so that the operator may remove the disposable cover without contacting the body 24 and the side portions 26 of the cover 10 which have potentially been exposed to dangerous or infectious microorganisms. The tab portions 28 of the best mode of the invention are attached to the outer edges of the side portion 26 of the conformable barrier 22.

Referring now to FIG. 2, for ease of handling, a removable holder 30 is provided so that the sterility of the barrier 22 is maintained while handling the barrier during deposition thereof. Further, the structure substantially provides for the exclusion of air from between the mounted barrier 22 and the face 18 of the prism 12. This enables the operator to ensure that air bubbles do not interfere with the visual indicia or mires of applanation of the tonometer. The best mode of practicing the current invention includes a carrier strip 32 for handling the conformable barrier 22 and a sealed envelope structure 34 for enclosing the conformable barrier 22. The carrier strip 32 is constructed for receiving the barrier 22 and has a release layer of adhesive about a central aperture 36. With the barrier in place and adhered to the carrier strip 32, the body portion 24 is aligned with the aperture 36. The carrier strip 32 is further constructed so that, with the barrier 22 thereon, the strip 32 extends sufficiently therebeyond to provide a handling means for the barrier 22. Thus, a person holding the carrier strip 32 can do so without touching the barrier 22. The envelope structure 34 is completed by an aperture cover 38 and a sterile seal 40. The aperture cover 38 is adhesively and releasably mounted to the carrier strip 32 on the side opposite the barrier 22 and the sterile seal 40 is adhesively and releasably mounted to the carrier strip 32 over and sealing barrier 22. While intact, the envelope structure 34 precludes microorganisms contacting the barrier 22. With the removal of the aperture cover 38 and the sterile seal 40, the carrier strip 32 and barrier 22 are so arranged that the barrier 22 is mountable on the prism 12 which is already assembled to the pressure arm 16. Optionally the carrier strip is structured to include a perforation 42 eminating from the aperture to the edge of the carrier strip 32 thereby upon mounting in place the conformable barrier 22 to the prism 12, the carrier strip 32 is removable from the pressure arm 16 by frangibly separating the carrier strip.

The technic of applanation tonometry is a method of scientifically poking a blunt stick in a patient's eye. The rationale for such intrusiveness is that, in order to monitor glaucoma and other eye diseases, it is necessary to measure accurately the intraocular pressure (IOP) and to observe carefully any changes with time of such measurements. In the Goldmann applanation tonometer, the "blunt stick" is a prism having a flat forwardly disposed face and a frustoconical rearwardly diverging side. The "poking" occurs during the measurement of the IOP at which time the prism is placed against the patient's cornea and the force or "poke" required to flatten the cornea is correlated with the fluid pressure therebehind. It has been found that this method is highly accurate and although somewhat more intrusive than other methods, it is the preferred diagnostic technic. In medical practice benefit is always measured against risks. All intrusions, no matter how limited, are measured against the risk, for example, of spreading communicable diseases, and particularly now of transmitting the human immunodeficiency virus. In view of the above and referring now to FIG. 3 in operation the present invention discloses a method employing sterile technics with an applanation tonometer. The method includes the steps of:

a. mounting a prism on the applanation tonometer;

b. installing a mechanical-barrier-type cover on said prism without contact between the barrier and the operator;

The above step may include one or more of the following substeps:

(1) removing the barrier and the carrier strip from the sterile packaging without touching the barrier;

(2) emplacing the body portion of the barrier on the face of the prism;

(3) conforming the side portion of the barrier to the side of the prism;

(4) removing the carrier strip from the barrier;

(5) inserting the prism through the aperture of the carrier strip;

(6) using the carrier, stretching the side portion of the barrier rearwardly along the side of the prism to resiliently mount the barrier thereon; and, (7) using the perforation, tearing the carrier strip from the tonometer;

The basic method continues with the following steps:

c. applanating the corneal area of eye of a patient a predetermined amount;

d. reading the tonometric measurement;

e. disengaging the tonometer from the eye of the patient;

f. demounting said cover without contact between the barrier and the operator:

The above step may include the following substeps:

(1) grasping the tab portions of the barrier attached to the outer edges of the side portions; and, (2) using the tab portion, outwardly stretching and forwardly pulling the barrier away from the prism without contacting the nonsterile portion of the barrier.

The method is concluded by the steps of:

g. safely disposing of the used cover; and, h. repeating steps a through g for each tonometric measurement.

By employing such sterile technic, any transfer of microorganisms from the eye of the patient to the applanation tonometer, to other patients, and to operators of the applanation tonometer is barred by the mechanical-barrier-effect of the disposable cover.

Although the best mode of the invention has been described herein in some detail, it has not been possible to include each and every variation. Those skilled in the art of applanation tonometers will be able to make slight variations in the mechanical arrangement suggested hereby without departing from the spirit of the invention and still be within the scope of the claims appended hereto.

What is claimed is:

1. A disposable cover for the prism of an applanation tonometer, said prism being a rearwardly diverging frustoconical configured member with a flat forwardly disposed face, said cover comprising:

a conformable barrier, in turn, comprising a body portion of a substantially optically transparent material for deposition upon said flat forwardly disposed face; and a side portion contiguous with said body portion, said side portion circumsiliently sealable to said rearwardly diverging member;

whereby said conformable barrier when mounted on said prism precludes the transfer of microorganisms from the eye of a patient to said prism during a tonometric examination without disturbing the viewing through the prism of the applanation tonometer.

2. A disposable cover as described in claim 1 wherein said cover further comprises:

said side portion having outer edges and, upon installation of said disposable cover, the outer edges being adjacent to the rearwardly diverging member;

tab portions attached to the outer edges of said side portion for facilitating the removal of the disposable cover without contact with the used said body and said side portions.

3. A disposable cover as described in claim 1 wherein said cover further comprises:

removable holder means for depositing said barrier upon said prism while substantially excluding air from between the barrier and the face of the prism.

4. A disposable cover as described in claim 3 wherein said removable holder means is a carrier strip releasably adhered on one side thereof to said barrier.

5. A disposable cover as described in claim 4 wherein said carrier strip further comprises:

aperture means for exposing said body portion and for receiving said face of said prism thereby enabling the deposition of therethrough said body portion upon said face.

6. A disposable cover as described in claim 5 wherein said carrier strip is frangible enabling deposition of the barrier onto the mounted prism and subsequent removal of the carrier strip without contact between the barrier and the installer thereof.

7. A disposable cover as described in claim 5 wherein said removable holder means further comprises:
an aperture cover removably secured to the carrier strip on the side opposite said barrier, said aperture cover being demountable without disturbing the barrier.

8. A disposable cover as described in claim 7 wherein said removable holder means further comprises:
a sterile seal attached to said carrier strip; and wherein said sterile seal, said carrier strip and said aperture cover form a sealed envelope about said barrier precluding contact thereby with microorganisms.

9. A disposable cover as described in claim 8 wherein said sealed envelope with said barrier therein are sterilizable without affecting the adhesion of the barrier to the carrier strip, the securement of the aperture cover to the carrier strip, and the attachment of the sterile seal to the carrier strip.

10. A sterile cover for the prism of an applanation tonometer for precluding the transfer of microorganisms from the eye of a patient to said prism during an examination and the transfer of microorganisms to the eye of the patient from said prism during an examination, said prism being a rearwardly diverging frustoconical configured member with a flat forwardly disposed face, said cover comprising:
a conformable barrier, in turn, comprising
a sterile body portion of a substantially optically transparent material for deposition upon said flat forwardly disposed face and
a sterile side portion contiguous with said body portion, said side portion circumsiliently sealable to said rearwardly diverging member;
tab portions attached to outer edges of said side portion for facilitating the removal of the disposable cover; and,
removable holder means for depositing said barrier upon said prism while substantially excluding air from between the barrier and the face of the prism;
whereby, prior to a tonometric examination, the sterile cover is deposited onto the prism without operator contact with the sterile body and side portions of the barrier, and, after a tonometric examination, the nonsterile cover is removed from the prism without the microorganisms thereon being transferred to the operator.

11. A disposable cover as described in claim 10 wherein said removable holder means is a carrier strip releasably adhered on one side thereof to said barrier.

12. A disposable cover as described in claim 11 wherein said carrier strip further comprises:
aperture means for exposing said body portion and for receiving therethrough said face of said prism thereby enabling the deposition of said body portion upon said face.

13. A disposable cover as described in claim 12 wherein said carrier strip is frangible enabling deposition of the barrier onto the mounted prism and subsequent removal of the carrier strip without contact between the barrier and the installer thereof.

14. A disposable cover as described in claim 12 wherein said removable holder means further comprises:
an aperture cover removably secured to the carrier strip on the side opposite said barrier, said aperture cover being demountable without disturbing the barrier.

15. A disposable cover as described in claim 14 wherein said removable holder means further comprises:
a sterile seal attached to said carrier strip; and wherein said sterile seal, said carrier strip and said aperture cover form a sealed envelope about said barrier precluding contact thereby with microorganisms.

16. A disposable cover as described in claim 15 wherein said sealed envelope with said barrier therein are sterilizable without affecting the adhesion of the barrier to the carrier strip, the securement of the aperture cover to the carrier strip, and the attachment of the sterile seal to the carrier strip.

17. A disposable cover assembly for the prism on an applanation tonometer, said prism being a rearwardly diverging frustoconical configured member with a flat forwardly disposed face, said cover assembly comprising:
a conformable barrier, in turn, comprising
a body portion of a substantially optically transparent material for deposition upon said flat forwardly disposed face; and
a side portion contiguous with said body portion, said side portion circumsiliently sealable to said rearwardly diverging member;
removable holder means for depositing said barrier upon said prism while substantially excluding air from between the barrier and the face of the prism, said removable holder means, in turn, comprising:
a carrier strip releasably adhered on one side thereof to said barrier,
aperture means for exposing said body portion and for receiving therethrough said face of said prism thereby enabling the deposition of said body portion upon said face,
an aperture cover removably secured to the carrier strip on the side opposite said barrier, said aperture cover being demountable without disturbing the barrier; and,
a sterile seal attached to said carrier strip; and wherein said sterile seal, said carrier strip and said aperture cover form a sealed envelope about said barrier precluding contact thereby with microorganisms.

18. A disposable cover as described in claim 17 wherein said cover further comprises:
tab portions attached to outer edges of said side portion for facilitating the removal of the disposable cover without contact with the used said body and said side portions.

19. A disposable cover as described in claim 17 wherein said carrier strip is frangible enabling deposition of the barrier onto the mounted prism and subsequent removal of the carrier strip without contact between the barrier and the installer thereof.

20. A disposable cover as described in claim 17 wherein said sealed envelope with said barrier therein are sterilizable without affecting the adhesion of the barrier to the carrier strip, the securement of the aperture cover to the carrier strip, and the attachment of the sterile seal to the carrier strip.

* * * * *